United States Patent
Gray

(10) Patent No.: US 11,097,021 B2
(45) Date of Patent: Aug. 24, 2021

(54) POLYMER BASED RADIONUCLIDE CONTAINING PARTICULATE MATERIAL

(71) Applicant: Sirtex Medical Limited, North Ryde (AU)

(72) Inventor: Bruce Nathaniel Gray, Claremont (AU)

(73) Assignee: Sirtex Medical Limited, North Ryde (AU)

( * ) Notice: Subject to any disclaimer, the term of this patent is extended or adjusted under 35 U.S.C. 154(b) by 0 days.

(21) Appl. No.: 16/280,171

(22) Filed: Feb. 20, 2019

(65) Prior Publication Data

US 2019/0175768 A1    Jun. 13, 2019

Related U.S. Application Data

(63) Continuation of application No. 13/968,921, filed on Aug. 16, 2013, now abandoned, which is a continuation of application No. 12/712,843, filed on Feb. 25, 2010, now abandoned, which is a continuation of application No. 11/743,530, filed on May 2, 2007, now abandoned, which is a continuation of application No. 10/173,496, filed on Jun. 17, 2002, now abandoned, which is a continuation of application No. PCT/AU01/01370, filed on Oct. 25, 2001.

(51) Int. Cl.
  *A61K 51/12* (2006.01)
  *A61K 51/06* (2006.01)

(52) U.S. Cl.
  CPC .......... *A61K 51/1251* (2013.01); *A61K 51/06* (2013.01); *A61K 51/1255* (2013.01)

(58) Field of Classification Search
  CPC .... A61K 51/00; A61K 51/06; A61K 51/1251; A61K 51/1255; A61K 2121/00; A61K 2123/00; A61K 51/02; A61K 51/12; A61K 51/22; A61K 51/1241; A61K 51/1244; A61P 1/16; B82Y 5/00; C01G 49/02; C01G 49/0018; C01G 49/0054; C30B 29/28; C30B 19/02; H01F 10/24; C01P 2002/52; C01P 2002/54; G02F 1/09
  USPC ...... 424/1.11, 1.29, 1.65, 9.1, 9.2, 400, 489, 424/490
  See application file for complete search history.

(56) References Cited

U.S. PATENT DOCUMENTS

| | | | |
|---|---|---|---|
| 3,127,313 A | 3/1964 | Glenn | |
| 4,108,972 A | 8/1978 | Dreyer | |
| 4,115,536 A | 9/1978 | Rothman et al. | |
| 4,789,501 A | 12/1988 | Day et al. | |
| 4,889,707 A | 12/1989 | Day et al. | |
| 4,891,164 A | 1/1990 | Gaffney et al. | |
| 5,011,797 A | 4/1991 | Day et al. | |
| 5,039,326 A | 8/1991 | Day et al. | |
| 5,320,824 A | 6/1994 | Brodack et al. | |
| 5,837,226 A | 11/1998 | Jungherr et al. | |
| 5,885,547 A * | 3/1999 | Gray | B01J 13/04 424/1.37 |
| 5,932,248 A | 8/1999 | Chen et al. | |
| 6,133,498 A | 10/2000 | Singh et al. | |
| 6,165,440 A | 12/2000 | Esenaliev | |
| 6,258,338 B1 | 7/2001 | Gray | |
| 6,358,531 B1 | 3/2002 | Day et al. | |
| 6,379,648 B1 | 4/2002 | Day et al. | |
| 6,455,024 B1 | 9/2002 | Glajch et al. | |
| 6,537,518 B1 | 3/2003 | Gray | |
| 6,998,105 B2 | 2/2006 | Ruys et al. | |
| 7,150,867 B2 | 12/2006 | Ruys et al. | |

FOREIGN PATENT DOCUMENTS

| | | |
|---|---|---|
| WO | 1985/002772 A1 | 7/1985 |
| WO | 1986/003124 A1 | 6/1986 |
| WO | 1995/019841 A1 | 7/1995 |
| WO | 1999/051278 A1 | 10/1999 |
| WO | 2000/044682 A9 | 8/2000 |
| WO | 2000069413 A1 | 11/2000 |
| WO | 2001034196 A2 | 5/2001 |
| WO | 2002030399 A2 | 4/2002 |

OTHER PUBLICATIONS

Chamberlain et al, Br. J. Surg., vol. 70, pp. 596-598. (Year: 1983).*
Stribley et al., "Internal Radiotherapy for Hepatic Metastases II: The Blood Supply to Hepatic Metastases", Journal of Surgical Research, 34(1):25-32 (Jan. 1983).
Self, "Yttrium-90 microspheres project—Experimental Procedures and Equipment." Department of Physiology & Department of Surgery, St. Vincent's Hospital, Univ. of Melbourne. 1983-1984, (28 pages).
Simon et al, Intra-Arterial Irradiation of Tumors, A Safe Procedure, Am J Roentgenol, 112(4):732-739 (Aug. 1971).
SIRTEX Medical Limited—Prospectus issued at Initial Public Offering for entry of SIRTEX Medical Limited on the Australian Stock Exchange. (2000).
SIRTEX Medical Limited—Extract from web page accessed on (May 22, 2009). http://www.sirtex.com/content.cfm?sec=aust_nz &ID=aust_nz.
Third Party Observations under Art. 115; Prior art relevant to European patent Application No. 01978015.4 (date not provided); Statuory Declaration, M. Burton.
Turner et al. "I66Ho-microsphere liver radiotherapy: a preclinical SPECT dosimetry study in the pig." Nuclear Medicine Communications, 15(7):545-553 (1994).

(Continued)

Primary Examiner — D. L. Jones
(74) *Attorney, Agent, or Firm* — Merchant & Gould P.C.

(57) ABSTRACT

The invention relates to a particulate material having a diameter in the range of from 5 to 200 microns comprising polymeric matrix stably incorporated radionuclide, processes for its production and method of radiation therapy utilising the particulate material.

4 Claims, 1 Drawing Sheet

(56) References Cited

OTHER PUBLICATIONS

Wang et al., "Intratumoral Injection of Rhenium-188 Microspheres into an Animal Model of Hepatoma", The Journal of Nuclear Medicine, 39, No. (JO):1752-1757 (1998).
Wollner et al., "Effects of Hepatic Arterial Yttrium-90 Microsphere Administration Alone and Combined with Regional Bromodeoxyuridine Infusion in Dogs", Cancer Research 47(12):3285-3290 (1987).
Yorke et al., "Can Current Models Explain the Lack of Liver Complications in Y-90 Microsphere Therapy?," Clinical Cancer Research, 5(Suppl.):3024s-3030s (Oct. 1989).
Zielinski et al., "Synthesis and Quality control testing of 32P Labeled Ion Exchange Resin Microspheres for Radiation Therapy of Hepatic Neoplasms", J. Appl. Radiat. Isot., 34(9):1343-1350 (1983).
Letter dated Jun. 17, 2009 from Australian Patent Office regarding a third party submission in Australian Application No. 2007202491.
Letter dated Mar. 29, 2010 from Australian Patent Office regarding a third party submission in Australian Application No. 2007202491.
Letter dated Nov. 29, 2010 from Australian Patent Office regarding a third party submission in Australian Application No. 2007202491.
Australia Patents Acts of 1990—Statutory Declaration dated Jun. 30, 2009.
Ariel et al., "Treatment of Inoperable cancer of the liver by intra-arterial radioactive isotopes and chemotherapy", Cancer, 20(5):793-804 (1967).
Ariel et al., "Treatment of Symptomatic Metastatic Cancer to the Liver from primary colon and rectal cancer by Intraarterial administration of Chemotherapy and radioactive isotopes", J. of Surgical Oncology, 10: 327-336 (1978).
Ariel et al., "Treatment of systematic metastatic cancer to the liver from primary colon and rectal cancer by the intra-arterial administration of chemotherapy and radioactive isotopes", Prog Clin Cancer 1978; 7:247-254 (1978).
Ariel et al., "Treatment of Asymptomatic Metastatic Cancer to the Liver From Primary Colon and Rectal Cancer by the Intraarterial Administration of Chemotherapy and Radioactive Isotopes", Journal of Surgical Oncology, 20:51-156 (1982).
Blanchard et al., "Treatment of Liver Tumors with Yttrium-90 Microspheres Alone", J. Can. Assoc. Radiol., 40:206-210 (1989).
Burton et al., "Manipulation of Experimental Rat and Rabbit Liver Tumor Blood Flow with Angiotension II", Cancer Research, 45(11.1):5390-5393 (1985).
Burton et al. Effect of angiotensin II on blood flow in the transplanted sheep squamous cell carcinoma, Europ. J. Cancer Clin. Oncol., 24(8): 1373-1376 (Aug. 1988).
Burton et al., "Selective Internal Radiation Therapy: Distribution of Radiation in the Liver", Eur. J. Cancer Clin. Oncol., 25(10)1487-1491 (1989).
Burton et al., "Intraoperative Dosimetry of 90Y in Liver Tissue", Nucl. Med. Biol., 16(5):495-498 (1989).
Burton et al., "Selective Internal Radiation Therapy: validation of Intraoperative Dosimetry," Radiology, 175(1):253-255 (Apr. 1990).
Caldarola et al., "Preparation of 32P labeled resin microspheres for radiation treatment of tumors by intra-arterial injection", Min. Nucl., 55:169-174 (1964).
Canadian Examination Report on application 2,426, 602 dated Sep. 6, 2011.
Chamberlain et al., "Hepatic metastases—a physiological approach to treatment", Br. J. Surg., 70(10):596-598 (1983).
Dogliotti et al., "New developments in the local treatment of tumors. Preliminary communication on the use of new P32 preparation", Panminerva Med., 4:465-466 (1962).
Einhom et al., "Radioactive Yttrium (Y00) as a possible adjunct in the treatment of papillomatosis of the urinary bladder", Acta Radiol., 43(4):298-304 (1955).
Erbe et al., "Chemical durability of Y203—Al203—Si02 glasses for the in vivo delivery of beta radiation", Journal of Biomedical Materials Research,.27:1301-1308 (1993).
European Examination Report on application 01 978 015 dated Nov. 16, 2011.
Fox et al., "Dose Distribution Following Selective Internal Radiation Therapy", Int. J. Radiation Oncology Biol. Phys., 21(2):463-467 (Jul. 1991).
Grady et al., "Internal Radiation Therapy of Liver Cancer. (90-Yttrium resin spheres intra-arterially to supplement external radiation therapy, local and systemic chemotherapy", J. Med. Assoc. Ga., 66(8):625-629 (1977).
Grady, "Case Report presented at the meeting of the American College of Nuclear Medicine. Intrahepatic Arterial 90-Yttrium Resin Spheres to Treat Liver Cancer", Int. J. Nucl. Med. Biol., 5(6):253-254 (1978).
Grady, "Internal Radiation Therapy of Hepatic Cancer", Dis Colon Rectum, 22(6):371-375 (Sep. 1979).
Gray et al., "Selective Internal Radiation (SIR) Therapy for Treatment of Liver Metastases: Measurement of Response Rate", J. of Surgical Oncology, 42(3):192-196 (Nov. 1989).
Gray et al., "Tolerance of the Liver to the Effects of Yttrium-90 Radiation", Int. J. Radiation Oncology Biol. Phys., 18(3):619-623 (Mar. 1990).
Gray et al., "Regression of Liver metastases following treatment with Yttrium-90 microspheres", Aust. N Z J Surg., 62(2)105-110 (1992).
Gray et al., "Treatment of Colorectal Liver Metastases with SIR-spheres plus chemotherapy." GI Cancer. 3(4):249-257 (2000).
Gray et al., "Distribution of Radioactive Microspheres in Liver Parenchyma and Tumour Tissue", Proceedings of the Surgical Research Society of Australasia, p. 366 (Date Unknown).
Herba et al., "Hepatic Malignacies: Improved Treatment with Intraarterial Y-90", Radiology, 169(2):311-314 (Nov. 1988).
Ho et al., "Partition Model for Estimating Radiation Doses from Yttrium-90 Microspheres in Treating Hepatic Tumours," European Journal of Nuclear Medicine, 23(8):947-952 (Aug. 1996).
Ho et al., "Clinical Evaluation of the Partition Model for Estimating Radiation Doses from Yttrium-90 Microspheres in the Treatment of Hepatic Cancer", European Journal of Nuclear Medicine, 24(3):293-298 (Mar. 1997).
Hetherington, "Clinical development of holmium 166 microspheres for therapy of hepatic metastases", International Atomic Energy Agency (IAEA) Report of 1999.
Houle et al., "Hepatocellular Carcinoma: Pilot Trial of Treatment with Y-90 Microspheres" Radiology, 172:857-860 (1989).
Johnson et al., "Chemotherapy and radiation Therapy", Hepatobiliary Malignancy—Its Multidisciplinary Management, ed. by J. Treblanche, (Jan. 15, 1994).
Kawashita et al. "Preparation of Glasses for Radiotherapy by Ion Implantation", Radiat. Phys. Chem., 46(2):269-274 (1995).
Kawashita et al., "Surface structure and chemical durability of P+-implanted Y203—Al203—Si02 glass for radiotherapy of cancer", Journal of Non-Crystalline Solids, 255:140-148 (1999).
Lau et al., "Therapeutic Aspects of Radioisotopes in Hepatobiliary Malignancy", Br. J. Surg., 79(7):711 (Jul. 1992).
Lau et al., "Treatment of Inoperable Hepatocellular Carcinoma with Intrahepatic Arterial Yttrium-90 Microspheres: a Phase I and II Study", Br. J. Cancer, 70:994-999 (1994).
Lau et al., "Selective Internal Radiation Therapy for Nonresectable Hepatocellular Carcinoma with Intraarterial Infusion of Yttrium Microspheres," I.J. Radiation Oncology, 40(3):583-592 (1998).
Mantravadi et al., Intraarterial Yttrium 90 in the treatment of hepatic malignancy Arch Otolaryngol, 108(2):108-111 (Feb. 1982).
Mantravadi et al., "Intraarterial Yttrium 90 in the treatment of hepatic malignancy." Radiology, 142(3):783-786 (Mar. 1982).
Meade. "The effect of sphere size on distribution of radioactive microspheres in experimental hepatic tumours," Department of Physiology & Department of Surgery, St. Vincent's Hospital, Univ. of Melbourne—Academic Thesis (1984).
Meade et al., "Distribution of Different Sized Microspheres in Experimental Hepatic Tumours", Eur. J. Cancer Clin. Oncol., 23(1):37-41 (1987).
Muller et al. "A new method for the treatment of cancer of the lungs by means of artificial radioactivity." Acta Radiol., 35(5-6):449-468 (1951).

(56) References Cited

OTHER PUBLICATIONS

Mullin, "Crystallisation." Butterworths & Co. Australia Ltd., pp. 174-232 (1972).
Nolan et al., "Regional internal radiation for hepatic cancer", Panminerva Med., 17(11-12):409-411 (1975).
Piovella et al., "The Behaviour of Rigid, Microscopic Resin Spheres in the Terminal Circulation of Tumours," 4th Europ. Conf. Microcirculation, 9:446-449 (1966).
Shepherd et al., "A Phase I Dose Escalation Trial of Yttrium-90 Microspheres in the Treatment of Primary Hepatocellular Carcinoma", Cancer, 70(9):2250-2254 (Nov. 1, 1992).

\* cited by examiner

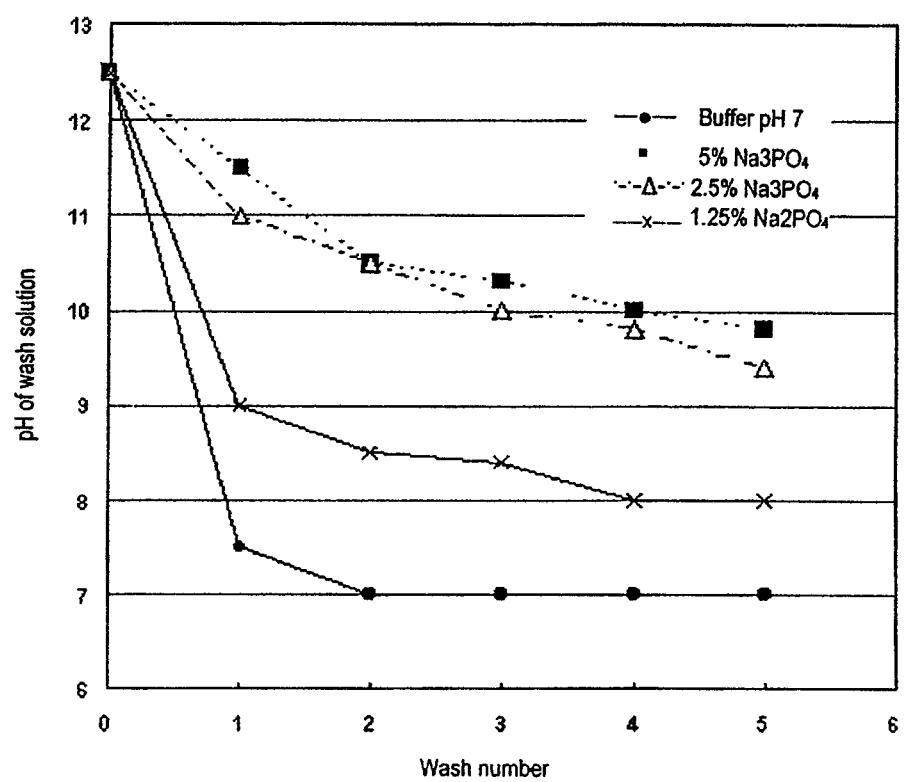

POLYMER BASED RADIONUCLIDE CONTAINING PARTICULATE MATERIAL

This application is a continuation of U.S. application Ser. No. 13/968,921, filed Aug. 16, 2013, which is a continuation of U.S. application Ser. No. 12/712,843 filed Feb. 25, 2010, which is a continuation of U.S. application Ser. No. 11/743,530, filed May 2, 2007, now abandoned, which is a continuation of U.S. application Ser. No. 10/173,496, filed Jun. 17, 2002, now abandoned, which is a continuation of PCT/AU01/01370, filed Oct. 25, 2001, now abandoned, which applications are incorporated herein by reference in their entirety.

FIELD OF THE INVENTION

This invention relates to a particulate material that comprises a polymer, particularly a polymer and a radionuclide, to a method for the production thereof, and to methods for the use of this particulate material.

In on particular aspect, this invention relates to micro spheres which comprise a polymer and a radionuclide such as radioactive yttrium, and to the use of these micro spheres in the treatment of cancer in humans and other mammals.

The particulate material of this invention is designed to be administered into the arterial blood supply of an organ to be treated, whereby it becomes entrapped in the small blood vessels of target organ and irradiates it. An alternate form of administration is to inject the polymer based particulate material directly into the target organ or a solid tumour to be treated.

The particulate material of the present invention therefore has utility in the treatment of various forms of cancer and tumours, but particularly in the treatment of primary and secondary cancer of the liver and the brain. It is to be understood that the particulate material of the invention is not limited to radioactive micro spheres, but may be extended to other radioactive polymeric particles which are suitable for use in the treatment methods described herein.

BACKGROUND OF THE INVENTION

Many previous attempts have been made to locally administer radioactive materials to patients with cancer as a form of therapy. In some of these, the radioactive materials have been incorporated into small particles, seeds, wires and similar related configurations that can be directly implanted into the cancer. When radioactive particles are administered into the blood supply of the target organ, the technique has become known as Selective Internal Radiation Therapy (SIRT). Generally, the main form of application of SIRT has been its use to treat cancers in the liver.

There are many potential advantages of SIR T over conventional, external beam radiotherapy. Firstly, the radiation is delivered preferentially to the cancer within the target organ. Secondly, the radiation is slowly and continually delivered as the radionuclide decays. Thirdly, by manipulating the arterial blood supply with vasoactive substances (such as Angiotensin-2), it is possible to enhance the percentage of radioactive particles that go to the cancerous part of the organ, as opposed to the healthy normal tissues. This has the effect of preferentially increasing the radiation dose to the cancer while maintaining the radiation dose to the normal tissues at a lower level (Burton, M. A. et al.; Effect of Angiotensin-2 on blood flow in the transplanted sheep squamous cell carcinoma. Europ. J. Cancer Clin. Oncol. 1988, 24(8):1373-1376).

When microspheres or other small particles are administered into the arterial blood supply of a target organ, it is desirable to have them of a size, shape and density that results in the optimal homogeneous distribution within the target organ. If the microspheres or small particles do not distribute evenly, and as a function of the absolute arterial blood flow, then they may accumulate in excessive numbers in some areas and cause focal areas of excessive radiation. It has been shown that micro spheres of approximately 25-50 micron in diameter have the best distribution characteristics when administered into the arterial circulation of the liver (Meade, V. et al.; Distribution of different sized micro spheres in experimental hepatic tumours. Europ. J. Cancer & Clin. Oncol. 1987, 23:23-41).

If the particles are too dense or heavy, then they will not distribute evenly in the target organ and will accumulate in excessive concentrations in areas that do not contain the cancer. It has been shown that solid, heavy microspheres distribute poorly within the parenchyma of the liver when injected into the arterial supply of the liver. This, in turn, decreases the effective radiation reaching the cancer in the target organ, which decreases the ability of the radioactive microspheres to kill the tumour cells. In contrast, lighter micro spheres with a specific gravity of the order of 2.0 distribute well within the liver (Burton, M. A. et al.; Selective International Radiation Therapy; Distribution of radiation in the liver. Europ. J. Cancer Clin. Oncol. 198, 25:1487-1491).

For radioactive particulate material to be used successfully for the treatment of cancer, the radiation emitted should be of high energy and short range. This ensures that the energy emitted will be deposited into the tissues immediately around the particulate material and not into tissues which are not the target of the radiation treatment. In this treatment mode, it is desirable to have high energy but short penetration beta-radiation which will confine the radiation effects to the immediate vicinity of the particulate material. There are many radionuclides that can be incorporated into microspheres that can be used for SIRT. Of particular suitability for use in this form of treatment is the unstable isotope of yttrium (Y-90). Yttrium-90 decays with a half life of 64 hours, while emitting a high energy pure beta radiation. However, other radionuclides may also be used in place of yttriwn-90 of which the isotopes of holmium, samarium, iodine, iridium, phosphorus, rhenium are some examples.

Ceramic particles have been produced that are either coated with or contain radionuclides. However, the presence of other radioactive substances that are not required for the radiation treatment of the target tissue, has then unwanted and deleterious radiation effects may occur. It is therefore desirable to have particulate material of such a composition that it only contains the single desired radionuclide.

In the earliest clinical use of yttrium-90 containing microspheres, the yttrium was incorporated into a polymeric matrix that was formulated into microspheres. While these micro spheres were of an appropriate density to ensure good distribution characteristics in the liver, there were several instances in which the yttrium-90 leached from the microspheres and caused inappropriate radiation of other tissues. Attempts to incorporate other radionuclides such as holmium into resin or polymer based materials have resulted in leaching of the radionuclide and this has resulted in severe consequences for the patients that have been treated with the product.

In one attempt to overcome the problem of leaching, a radioactive microsphere comprising a biologically compatible glass material containing a beta- or gamma-radiation emitting radioisotope such as yttrium-90 distributed throughout the glass, has been developed (International Patent Publication No. WO 86/03124). These microspheres are solid glass and contain the element yttrium-89 that can be activated to the radionuclide yttrium-90 by placing the micro spheres in a neutron beam. These glass micro spheres have several disadvantages including being of a higher specific gravity than is desirable and containing other elements such as alumina and silica which are activated to undesirable radionuclides when placed in a neutron beam.

Another approach has been focused on the use of small hollow or cup-shaped ceramic particles or microspheres, wherein the chemic base material consists or comprises yttria or the like (International Patent Publication No. WO 95/19841). These micro spheres were developed to overcome the problem of high density associated with the solid glass microspheres described in International Patent Publication No. WO86/03124.

SUMMARY OF THE INVENTION

In one aspect the present invention provides a particulate material having a diameter in the range of from 5 to 200 microns comprising a polymeric matrix and a stably incorporated radionuclide.

In another aspect, the invention provides a process for the production of a particulate material having a diameter in the range of from 5 to 200 microns comprising the step of combining a polymeric matrix and a radionuclide for a time and under conditions sufficient to stably incorporate the radionuclide in the matrix to produce a particulate material having a diameter in the range of from 5 to 200 microns.

In another aspect, the present invention provides a method of radiation therapy of a patient, which comprises administration to the patient of a particulate material having a diameter in the range of from 5 to 200 microns comprising a polymeric matrix and a stably incorporated radionuclide.

The present invention also provides for the use of particulate material having a diameter in the range of from 5 to 200 microns comprising a polymeric matrix and a stably incorporated radionuclide in the radiation therapy of a patient.

BRIEF DESCRIPTION OF THE DRAWINGS

Further objected and advantages of the present invention will be more fully appreciated from a reading of the detailed description when considered with the accompanying drawing wherein:

FIG. 1 depicts pH results when the phosphate concentration the solution used to precipitate the radionuclide was varied; FIG. 1 further shows pH results measured when a 10 microsphere suspension is washed with a phosphate buffer having pH of 7.

DETAILED DESCRIPTION OF THE INVENTION

As used herein, references to the radionuclide being stably incorporated into particulate material or polymeric matrix are to be understood as referring to incorporation of the radionuclide so that it does not substantially leach out of the particulate material under physiological conditions such as in the patient or in storage. In a preferred embodiment the radionuclide is incorporated by precipitation into a polymeric matrix.

The leaching of radionuclides from the polymeric matrix can cause non-specific radiation of the patient and damage surrounding tissue. Preferably the amount of leaching is less than 5%, more preferably less than 4%, 3%, 2%, 1% or 0.4%. One method of assessing leaching is by adjusting a sample to pH 7.0 and agitating in a water bath at 37° C. for 20 minutes. A 100 µL sample is counted for beta emission in a Geiger-Muller counter. Another representative 100 µL sample is filtered through a 0.22 µm filter and the filtrate counted for beta emission in the Geiger-Muller counter. The percent unbound radionuclide is calculated by:

$$\frac{FiltrateCount}{SampleCount} \times 100 = \% \ UnboundRadionuclide$$

The radionuclide can be stably incorporated into the polymeric matrix by precipitating it as an insoluble salt. Where the radionuclide used is yttrium-90 the yttrium is preferably precipitated as a phosphate salt. However the present invention also extends to precipitation of the radionuclide as other insoluble salts including, for example, carbonate and bicarbonate salts. The radionuclide which is incorporated into the polymeric matrix in accordance with the present invention is preferably yttrium-90, but may also be any other suitable radionuclide which can be precipitated in solution, of which the isotopes of holmium, samarium, iodine, phosphorous, iridium and rhenium are some examples.

In a preferred embodiment the particulate material is a microsphere. The term microsphere is used in this specification as an example of a particulate material, it is not intended to limit the invention to microspheres, as the person skilled in the art will appreciate that the shape of the particulate material while preferably without sharp edges or points that could damage the patients arteries or catch in unintended locations, is not limited to spheres. Nor should the term microsphere be limited to spheres. Preferably the particulate material is substantially spherical, but need not be regular or symmetrical in shape.

In a preferred embodiment the polymeric matrix is partially cross linked. Preferably there is about 1% to about 20% cross linking, preferably about 2% to 10% cross linking and more preferably about 4% cross linking.

In particular, the present invention provides a particulate material as described above in which the polymeric matrix is an ion exchange resin, particularly a cation exchange resin. Preferably the ion exchange resin comprises a partially cross linked aliphatic polymer, including polystyrene. One particularly preferred cation exchange resin is the styrene/divinylbenzene copolymer resin commercially available under the trade name Aminex 50W-X4 (Biorad, Hercules, Calif.). However, there are many other commercially available cation exchange resins which are suitable.

When small particles are administered into the arterial blood supply of a target organ, it is desirable to have them of a size, shape and density that results in the optimal homogeneous distribution within the target organ. If the small particles do not distribute evenly then they may accumulate in excessive numbers in some areas and cause focal areas of excessive radiation. The particulate material is preferably low density, more particularly a density below 3.0 g/cc, even more preferably below 2.8 g/cc, 2.5 g/cc, 2.3 g/cc, 2.2 g/cc or 2.0 g/cc. The ideal particle for injection into the blood stream would have a very narrow size range with a SD of less than 5%, so as to assist in even distribution of the micro spheres within the target organ, particularly within the liver and would be sized in the range 5-200 micron preferably 15-100 micron and preferably 20-50 micron, and most preferably 30-35 micron.

It is also desirable to have the particulate material manufactured so that the suspending solution has a pH less than 9. If the pH is greater than 9 then this may result in irritation of the blood vessels when the suspension is injected into the artery or target organ. Preferably the pH is less than 8.5 or 8.0 and more preferably less than 7.5.

The present invention particularly provides a method for the production of a radioactive particulate material comprising a polymeric matrix as described above, characterised by the steps of;
(i) absorbing a radionuclide onto an ion-exchange resin particulate material having a diameter in the range of 20 to 50 microns and a specific gravity of less than 2.5; and
(ii) precipitating the radionuclide as an insoluble salt to stably incorporate the radionuclide into the particulate material.

In a preferred embodiment, the method of the present invention is carried out by firstly irradiating yttria (yttrium oxide) in a neutron beam to activate yttria to the isotope yttrium-90. The yttrium-90 oxide is then solubilised, for example as yttrium-90 sulphate solution. The ion exchange resin is preferably provided in the form of an aqueous slurry of micro spheres of ion exchange resin having a particle size 30 to 35 microns, and the yttrium-90 sulphate solution is added to the slurry to absorb the yttrium-90 into the ion exchange resin microspheres. Subsequently, the yttrium-90 is precipitated as a phosphate salt, for example by addition of tri-sodium phosphate solution, to stably incorporate the yttrium-90 into the microspheres. The particulate material may be combined with a solution of the radionuclide or the salt of the radionuclide may be combined with the particulate matter, in a solution suitable for solubilising the radionuclide.

Alternate sources of yttrium-90 may be used in the production of these microspheres. For example, a highly pure source of yttrium-90 may be obtained by extracting yttrium-90 from a parent nuclide and using this extracted yttrium-90 as the source of the soluble yttrium salt 25 that is then incorporated into the polymeric matrix of the microspheres.

In order to decrease the pH of the suspension containing the microspheres for injection into patients the micro spheres may be washed to remove any un-precipitated or loosely adherent radionuclide. The present invention provides a suspension of the required pH by precipitating the yttrium with a tri-sodium phosphate solution at a concentration containing at least a three-fold excess of phosphate ion, but not exceeding a 30-fold excess of phosphate ion, and then washing the microspheres with de-ionised water. Another approach which ensures that the pH of the micro sphere suspension is in the desired range is to wash the resin with a phosphate buffer solution of the desired pH.

The present invention also provides a method of radiation therapy of a human or other mammalian patient that comprises administration to the patient of particulate material as described above. The person skilled in the art will appreciate the administration may be by any suitable means and preferably by delivery to the relevant artery. For example in treating liver cancer, administration is preferably by laparotomy to expose the hepatic artery or by insertion of a catheter into the hepatic artery via the femoral, or brachial artery. Pre or co-administration of another agent may prepare the tumour for receipt of the particulate material, for example a vasioactive substance, such as angiotension-2 to redirect arterial blood flow into the tumour. Delivery of the particulate matter may be by single or multiple doses, until the desired level of radiation is reached.

Throughout this specification, unless the context requires otherwise, the word "comprise", and or variations such as "comprises" or "comprising", will be understood to imply the inclusion of a stated integer or step or group of integers or steps but not the exclusion of any other integer or step or group of integers or steps.

Further features of the present invention are more fully described in the following Examples. It is to be understood, however, that this detailed description is included solely for the purposes of exemplifying the present invention, and should not be understood in any way as a restriction on the broad description of the invention as set out above.

Example 1

Yttrium (90Y) labelled microspheres are made in the form of a sterile, pyrogen free suspension of resin beads labelled with yttrium (90Y) phosphate. The resin beads consist of sulphuric acid groups attached to a styrene divinylbenzene copolymer lattice.

Yttrium oxide is irradiated to produce yttrium-90 from the nuclear reaction Y-89 (n, γ) Y-90. Yttrium-90 has a half life of 64 hours. The yttrium (90Y) oxide is then dissolved in O.IM sulphuric acid with gentle heating and stirring to form a clear, colourless solution of yttrium (90Y) sulphate.

Symmetrical microspheres of ion exchange resin (Aminex 50W-X4 cation exchange resin; supplied by 'Bio-Rad Cat #1474313') with a diameter of approximately 30 to 35 microns are added to water (Water for Injections BP) to form a slurry that is then transferred into a reaction vessel. yttrium (90Y) sulphate solution is added to the reaction vessel and the mixture stirred at a speed sufficient to ensure homogeneity to absorb the yttrium (90Y) solution into the resin based microspheres. Tri-sodium phosphate solution (1.25% w/v) is then added to the reaction vessel with further stirring to precipitate the radionuclide as yttrium (90Y) phosphate.

The microspheres are then washed with a phosphate buffer solution until the pH of the wash solution is less than 9 and preferable less than 8.5. Following washing of the microspheres with water (Water for Injection BP), the microspheres are resuspended and diluted (if necessary) with water (Water for Injections BP) to give a light brown suspension having an activity of 3000 MBq 10%.

The resin-based yttrium microspheres produced by the above method have 0.01-0.4% unbound or unprecipitated 90Y when tested in the following leaching test:

A 5 μL sample is diluted with water to 5 mL, adjusted to pH 7.0 and agitated in a water bath at 37° C. for 20 minutes. A 100 μL sample is counted for beta emission in a Geiger-Muller counter. Another representative 100 μL sample is filtered through a 0.22 μm filter and the filtrate counted for beta emission in the Geiger-Muller counter. The percent unbound 90Y is calculated by:

$$\frac{FiltrateCount}{SampleCount} \times 100 = \%\ Unbound\ ^{90}Y$$

Example 2

The effect of phosphate concentration in the precipitation solution, and the effects of washing with phosphate buffer on the pH of a microsphere suspension are shown in the attached FIG. 1 which sets out the results of a number of experiments.

Example 3

The technique of Selective Internal Radiation Therapy (SIRT) has been described above. It involves either a laparotomy to expose the hepatic arterial circulation or the insertion of a catheter into the hepatic artery via the femoral, brachial or other suitable artery. This may be followed by the infusion of Angiotensin-2 into the hepatic artery to redirect arterial blood to flow into the metastatic tumour component of the liver and away from the normal parenchyma This is followed by embolisation of resin based yttrium-90 containing micro spheres (produced in accordance with Example 1) into the arterial circulation so that they become lodged in the microcirculation of the tumour. Repeated injections of micro spheres are made until the desired radiation level in the normal liver parenchyma is reached. By way of example, an amount of yttrium-90 activity that will result in an inferred radiation dose to the normal liver of approximately 80 Gy may be delivered. Because the radiation from SIRT is delivered as a series of discrete point sources, the dose of 80 Gy is an average dose with many normal liver parenchymal cells receiving much less than that dose.

The measurement of tumour response by objective parameters including reduction in tumour volume and serial estimations of serum carcino-embryonic antigen (CEA) levels, is an acceptable index of the ability of the treatment to alter the biological behaviour of the tumour.

The invention claimed is:

1. A process for the production of a particulate material having a diameter in the range of from 5 to 200 microns comprising a polymeric matrix and a radionuclide, the process comprising the steps of:
solubilizing the radionuclide in a solubilisation solution,
preparing a slurry of the polymeric matrix in water,
transferring the slurry to a reaction vessel and adding the solubilized radionuclide to the reaction vessel,
mixing the slurry of the polymeric matrix and the radionuclide until homogenous, and
precipitating the radionuclide as a phosphate salt by the addition of tri-sodium phosphate solution, wherein the radionuclide is stably incorporated such that there is less than 0.4% unbound or unprecipitated radionuclide, and wherein the resulting particulate material has an activity of 3000 MBq.

2. The process according to claim 1 wherein the radionuclide is stably incorporated by precipitation into the polymeric matrix.

3. The process according to claim 1 wherein the radionuclide is yttrium-90.

4. The process according to claim 1 wherein the polymeric matrix is an ion exchange resin.

* * * * *